(12) United States Patent
Moshinsky

(10) Patent No.: US 10,285,681 B2
(45) Date of Patent: May 14, 2019

(54) APPARATUS FOR COVERING AN EXPOSED END OF A SEVERED STERNUM

(71) Applicant: PROTEGO MEDICAL PTY LIMITED, Melbourne, Victoria (AU)

(72) Inventor: Randall Moshinsky, Victoria (AU)

(73) Assignee: PROTEGO MEDICAL PTY LIMITED, Melbourne, Victoria (AU)

( * ) Notice: Subject to any disclaimer, the term of this patent is extended or adjusted under 35 U.S.C. 154(b) by 0 days.

(21) Appl. No.: 14/399,875

(22) PCT Filed: May 7, 2013

(86) PCT No.: PCT/AU2013/000469
§ 371 (c)(1),
(2) Date: Nov. 7, 2014

(87) PCT Pub. No.: WO2013/166547
PCT Pub. Date: Nov. 14, 2013

(65) Prior Publication Data
US 2015/0148614 A1    May 28, 2015

(30) Foreign Application Priority Data
May 8, 2012  (AU) .................................. 2012901880

(51) Int. Cl.
*A61B 17/00* (2006.01)
*A61B 17/02* (2006.01)
(Continued)

(52) U.S. Cl.
CPC ...... *A61B 17/0218* (2013.01); *A61B 17/0206* (2013.01); *A61B 17/68* (2013.01);
(Continued)

(58) Field of Classification Search
CPC ....... A61B 19/00; A61B 1/32; A61B 17/8085; A61B 17/823; A61B 17/8076;
(Continued)

(56) References Cited

U.S. PATENT DOCUMENTS 3,882,855 A * 5/1975 Schulte .................. A61B 17/02
600/203
4,889,107 A * 12/1989 Kaufman ............... A61B 17/02
600/206
(Continued)

FOREIGN PATENT DOCUMENTS

JP    S577509 U    1/1982
JP    H03502169 A    5/1991
(Continued)

OTHER PUBLICATIONS

International Search Report dated Jun. 12, 2013 for International Application No. PCT/AU2013/000469.
(Continued)

*Primary Examiner* — Keri J Nelson
*Assistant Examiner* — Adam Baker
(74) *Attorney, Agent, or Firm* — Faegre Baker Daniel LLP

(57) ABSTRACT

The invention comprises an apparatus (10) for covering an exposed end of a severed sternum, comprising a strip (12) operative to cover the exposed end and pliable portions (14) which are able to be manually deformed over sides of the exposed end so as to retain the strip (12) against the exposed end to stop or at least reduce flow of blood from the exposed end.

20 Claims, 9 Drawing Sheets

(51) Int. Cl.
*A61B 17/12* (2006.01)
*A61B 17/68* (2006.01)
*A61B 17/80* (2006.01)

(52) U.S. Cl.
CPC ....... *A61B 17/8076* (2013.01); *A61B 17/8085* (2013.01); *A61B 2017/00946* (2013.01); *A61B 2017/0212* (2013.01); *A61B 2017/0225* (2013.01); *A61B 2017/0237* (2013.01); *A61B 2017/12004* (2013.01)

(58) Field of Classification Search
CPC ............ A61B 17/0206; A61B 17/0218; A61B 2017/12004; A61B 2017/0237; A61B 2017/0225; A61B 2017/0212; A61B 2017/00946; A61B 17/02; A61B 17/0293; A61B 17/68; A61B 2017/000946; A61F 13/00
USPC ....... 600/201, 207, 208, 209, 210, 211, 212, 600/213, 214, 215; 606/60, 151, 153, 606/191, 286, 298, 905, 907, 910; 604/290, 48; 128/887, 888, 897
See application file for complete search history.

(56) References Cited

U.S. PATENT DOCUMENTS

| | | | | |
|---|---|---|---|---|
| 5,474,094 A * | 12/1995 | Ellenberg, III | ........ | A61B 16/00 128/888 |
| 6,254,532 B1 * | 7/2001 | Paolitto | ............. | A61B 17/0206 600/201 |
| 6,312,377 B1 * | 11/2001 | Segermark | ............ | A61B 17/02 600/201 |
| 7,008,392 B2 * | 3/2006 | Beaudry | ................. | A61F 13/38 604/1 |
| 7,294,103 B2 * | 11/2007 | Bertolero | ............... | A61B 17/02 600/201 |
| 7,563,267 B2 * | 7/2009 | Goldfarb | ............... | A61B 50/30 606/151 |
| 2004/0186354 A1 * | 9/2004 | LiDonnici | ................ | A61B 1/32 600/210 |
| 2007/0075023 A1 * | 4/2007 | Wallace | .................. | A61F 13/10 210/672 |
| 2007/0255238 A1 * | 11/2007 | Cochrum | .......... | A61F 13/00034 604/290 |
| 2008/0215054 A1 * | 9/2008 | Wright | ................. | A61B 17/823 606/60 |
| 2009/0287060 A1 * | 11/2009 | Pell | ........................ | A61B 17/02 600/201 |
| 2012/0088961 A1 * | 4/2012 | Deasey | .................. | A61B 17/02 600/37 |
| 2013/0237769 A1 * | 9/2013 | Puskas | ..................... | A61B 1/32 600/232 |
| 2014/0303664 A1 * | 10/2014 | Beck | ...................... | A61B 17/02 606/191 |

FOREIGN PATENT DOCUMENTS

| | | |
|---|---|---|
| JP | 2009261811 A | 11/2009 |
| WO | 2008029367 A2 | 3/2008 |
| WO | 2010132558 A1 | 11/2010 |

OTHER PUBLICATIONS

Written Opinion of the International Search Authority dated Jun. 12, 2013 for International Application No. PCT/AU2013/000469.
First Office Action for Chinese Patent Application No. 201380023618.3 dated Jan. 5, 2016.
Office Action for Chinese Patent Application No. 201380023618.3 dated Jul. 14, 2016.
Patent Examination Report No. 1 for Australian Patent Application No. 2013258869.
International Preliminary Report on Patentability issued in PCT/AU2013/000469, dated Nov. 20, 2014, 6 pages.
European Search Report and Written Opinion for European Application No. 13787219.8 dated Jan. 11, 2016.
Examination Report for Japanese Application No. 2015-510574 dated Jan. 17, 2017.

* cited by examiner

Section A - A

APPARATUS FOR COVERING AN EXPOSED END OF A SEVERED STERNUM

CLAIM FOR PRIORITY

This application is the National Stage of International Application No. PCT/AU2013/000469, filed May 7, 2013, which in turn claims priority to and benefit of Australian Patent Application No. AU 2012901880, filed May 8, 2012. The entire contents of the aforementioned applications are herein expressly incorporated by reference.

FIELD OF THE INVENTION

The present invention relates to cardiac surgery and, more particularly, to an apparatus for covering an exposed end of a severed sternum to stem bleeding therefrom.

BACKGROUND OF THE INVENTION

Bleeding from an exposed sternal end which was created by a median sternotomy incision results in blood being shed into the pericardium and pleural cavity. This bleeding is from both the cortical and medullary bone of both sections. Cortical bleeding can be controlled with the use of a diathermy device, however, bleeding from the medullary bone is more difficult to control.

Blood in the pericardium and pleural cavity obstructs visibility during surgical procedures. This blood is either returned to the heart lung machine via a cardiotomy return sucker or collected with a cell-saver unit. However, blood which has come into contact with the pericardial or pleural surfaces and is returned to the circulation via a cardiotomy return sucker will elicit a detrimental inflammatory response to the patient. Blood returned to the circulation via the cell-saver circuit will result in loss of valuable dotting factors and platelets.

Bleeding from the sternum during the operation and in particular at the completion of the procedure makes it more difficult to determine if there are significant other bleeding sources present within the mediastinum or pericardium. The attribution of mediastinal and pericardial blood at the completion of the operation to bleeding from the sternum is a common cause for missed surgical bleeding sites. This results in an increased incidence of reoperation for bleeding. This in turn is associated with an increased sternal wound infection risk.

Also, ongoing blood loss from the sternum post-operatively (once the patient is in the intensive care unit) makes it difficult to differentiate sternal bleeding from significant mediastinal bleeding sites. The above problems contribute to a higher blood transfusion requirement.

Furthermore, sternal retractors placed directly in contact with the sternum can lead to sternal fractures. As the retractor is opened, the distribution of force is usually at the point of contact of 2 to 3 blades on either side rather than being distributed over the entire length of the sternum more evenly, leading to concentrated loading and fractures.

Previous proposals to deal with bleeding from the sternal medullary bone include using bone wax to cover the exposed end and the application of topical haemostatic agents or absorbable haemostats.

Bone wax can be ineffective and the introduction of a permanent foreign body into the sternal medullar is undesirable. In this regard, surgeons can be reluctant to place a permanent foreign body into the sternal medullar due to potential risk of increasing infection rate or making infection more difficult to treat if it occurs. There is also some evidence to suggest that bone wax inhibits osseous fusion and promotes infections.

Furthermore, inserting bone wax into the sternal medullar in elderly patients with soft sternal medullar is extremely ineffective in improving sternal haemostasis and elderly patients make up a large proportion of patients undergoing cardiac surgery.

Topical haemostatic agents or absorbable haemostats can be difficult and cumbersome to apply, messy and ineffective in achieving sternal haemostasis.

It has been previously proposed to provide a cover for the exposed sternal end. One example is shown in U.S. Patent Application No. 2008/0215054 (Wright). This document discloses a U-shaped device comprising an end wall and opposed walls which surround the upper and lower surfaces of the sternum. The device is formed from a biocompatible plastic, hard elastomer or metal such as stainless steel, aluminium, titanium or other suitable metal. As the device is rigid, it is ineffective at forming a tight seal against the exposed sternal end of a patient whose cut sternum does not match the configuration of the device.

One problem with previous proposals is that the sternums of individual patients are differently sized and shaped and this makes it difficult to provide a solution which is adaptable for different patients. In this regard, the length, width and curvature of respective sternums can vary significantly from one patient to the next.

Previous proposals for stemming bleeding from an exposed end of a severed sternum have not adequately accounted for sternum size variations and it is not practical to manufacture covers in the vast number of sizes that would be required.

Embodiments of the invention seek to solve, or at least ameliorate, one or more disadvantages of previous methods and apparatuses for stemming bleeding from an exposed end of a severed sternum.

SUMMARY OF THE INVENTION

According to the present invention, there is provided an apparatus for covering an exposed end of a severed sternum, comprising a strip operative to cover the exposed end and manually pliable portions which are able to be deformed over sides of the exposed end so as to retain the strip against the exposed end to stop or at least reduce flow of blood from the exposed end.

Preferably, the apparatus is generally planar and the pliable portions extend outwardly from the strip.

The strip can have a substantially rigid longitudinally extending central portion from which the pliable portions extend.

Preferably, the pliable portions are in the form of a skirt. Preferably, the pliable portions can be bent at any location along their length or across their extent so as to adapt to differently sized and/or shaped sternums.

Preferably, the apparatus further comprises a layer of haemostatic material which is arranged to be received against the exposed sternal end. The haemostatic material can be formed from an oxidised cellulose polymer.

The apparatus can further comprise a compressible layer between the haemostatic material and the strip to promote apposition between the haemostatic material and the exposed sternal end.

Preferably, the substantially rigid portion is configured for transferring a force from a retractor to maintain separation of opposing ends of the severed sternum.

Preferably, the rigid portion distributes force from the retractor across the exposed end to reduce fracturing of the sternum.

Preferably, the apparatus further comprises an intermediate hinge to provide for longitudinal flexing of the apparatus. Preferably, the hinge is disposed in a location generally corresponding to the manubriosternal joint of the sternum. Preferably, the pliable portions are necked in about the hinge.

Preferably, the apparatus is constructed in layers. Preferably, the strip is of unitary construction.

According to preferred embodiments, the strip and pliable portions are formed as an integral unit. Preferably, the integral unit is formed from aluminium sheet. Alternatively, the integral unit can be formed of a pliable mesh material. Preferably, the pliable mesh is formed of a metallic material.

According to preferred embodiments, the strip and the pliable portions, which may or may not be integrally formed, are encapsulated in a polymer cover. In some embodiments, the strip and the pliable portions may be encapsulated separately and joined once covered. Preferably, the polymer is silicone.

According to the present invention, there is also provided a method of reducing bleeding from an exposed end of a severed sternum, comprising the steps of: providing an apparatus having a strip and pliable retaining elements, the strip being operative to cover the exposed end; placing the strip against the exposed end; and plastically deforming the retaining elements over sides of the exposed end to retain the strip against the exposed end to stop or at least reduce flow of blood from the exposed end.

The method can further comprise the step of measuring the exposed end and selecting a pair of appropriately sized apparatuses from a selection of differently sized apparatuses. Preferably, the selection includes 2 to 4 differently sized apparatuses. Preferably the exposed end is measured using a sterilised disposable ruler. Alternatively, the apparatus may be provided in the form of a strip which can be cut to length depending on the size of a patient's sternum.

BRIEF DESCRIPTION OF THE DRAWINGS

Preferred embodiments of the invention will be further described, by way of non-limiting example only, with reference to the accompanying drawings in which.

Figure 1:
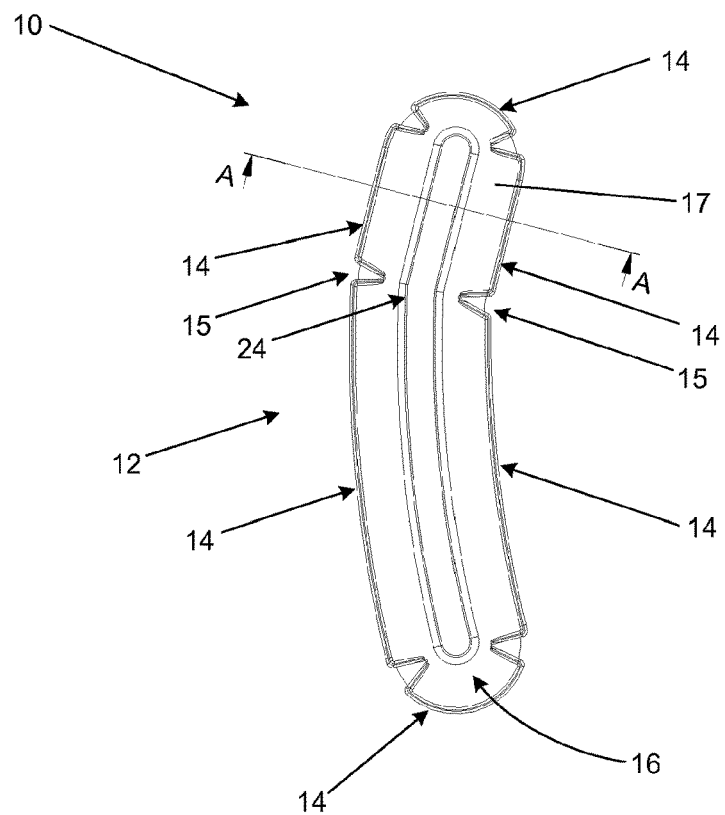
FIG. 1 is a plan view of an apparatus for covering an exposed end of a severed sternum of one embodiment of the invention.

It will be appreciated by those of relevant skill that the figures are not necessarily to scale, with some features exaggerated or minimised to show details of particular components.

Like numerals in the drawings refer to like parts.

DETAILED DESCRIPTION

In the following discussion and in the claims that follow, the term "invention" and the like mean "the one or more inventions disclosed in this application", unless expressly specified otherwise.

The terms "an embodiment", "embodiment", "embodiments", "the embodiment", "the embodiments", "one or more embodiments", "some embodiments", "certain embodiments", "one embodiment", "another embodiment", "alternative embodiment" and the like mean "one or more (but not all) embodiments of the disclosed invention(s)", unless expressly specified otherwise. A reference to "another embodiment" in describing an embodiment does not imply that the referenced embodiment is mutually exclusive with another embodiment (e.g., an embodiment described before the referenced embodiment), unless expressly specified otherwise.

Numerous references to a particular embodiment does not indicate a disclaimer or disavowal of additional, different embodiments, and similarly references to the description of embodiments which all include a particular feature does not indicate a disclaimer or disavowal of embodiments which do not include that particular feature. A clear disclaimer or disavowal in the present application shall be prefaced by the phrase "does not include" or by the phrase "cannot perform".

The terms "including", "comprising" and variations thereof mean "including but not limited to", unless expressly specified otherwise. The terms "a", "an" and "the" mean "one or more", unless expressly specified otherwise. The term "plurality" means "two or more", unless expressly specified otherwise.

The functionality and/or the features of a single device or component that is described may be alternatively embodied by one or more other devices or components which are described but are not explicitly described as having such functionality/features. Thus, other embodiments need not include the described device or component itself, but rather can include the one or more other devices or components which would, in those other embodiments, have such functionality/features.

No embodiment of method steps or device elements described in the present application constitutes the invention claimed herein, or is essential to the invention claimed herein, or is coextensive with the invention claimed herein, except where it is either expressly stated to be so in this specification or expressly recited in a claim.

The preambles of the claims that follow recite purposes, benefits and possible uses of the claimed invention only and do not limit the claimed invention.

The present disclosure is not a literal description of all embodiments of the invention(s). Also, the present disclosure is not a listing of features of the invention(s) which must be present in all embodiments.

Turning now to FIG. 1, there is shown an apparatus 10 according to a preferred embodiment of the present invention. The apparatus 10 is configured for covering an exposed end of a severed sternum of a patient.

The apparatus 10 includes a strip 12 which is operative to cover the exposed end and pliable portions or sections 14 which are bendable or able to be deformed over sides of the exposed end so as to retain or clamp the strip 12 against the exposed end to stop or at least reduce flow of blood from the exposed end, thereby promoting haemostasis. The pliable portions 14 are flexible and plastically deformable so as to be formable to the contour of differently sized and/or shaped sternums. The pliable portions 14 are manually deformable, thereby aiding the rapid deployment of the apparatus by a surgeon or other medical personnel. The strip 12 and the pliable portions 14 may be integrally formed, as illustrated, or they may be formed as separate elements.

The strip 12 is generally planar and is configured so that bringing it into contact with the exposed end of a severed sternum covers the exposed end to stop, or at least significantly reduce, bleeding from the exposed end.

The pliable portions 14 extend outwardly from the strip 12 so that in a resting, unused state the apparatus 10 is generally flat so as to simplify packaging and storage. The pliable portions 14 act as retaining or clamping elements and extend from the strip 12 a predetermined amount which is sufficient to provide adequate retention force to act as jaws that lock onto the sternum to maintain the apparatus in position when fixed to a sternal half. In the described preferred embodiment, the pliable portions 14 extend between 10 and 12 mm from the strip 12. The retaining force imparted onto the sternal half from the pliable portions once bent will be dependent on the properties of the material used for the strip and the desired amount of retaining or clamping force. As such, the length of the pliable portions 14 will vary depending on the construction of the apparatus and its intended application, but it is envisaged that an apparatus having pliable portions 14 that extend between 5 and 20 mm from the strip 12 would be suitable in most circumstances.

The sternums of different patients will be differently sized and shaped. In this regard, the length, width and curvature of respective sternums can vary significantly from one patient to the next. The pliable portions 14 can be bent at any location along their length or across their extent so as to adapt to differently sized and/or shaped sternums. In the illustrated embodiment, a plurality of pliable portions 14 are provided around sides of the apparatus 10 so that the apparatus 10 can be more easily moulded to the particular shape of a patient's sternum. It will also be appreciated that suitable performance may be achieved with pliable portions that are continuous and are in the form of a skirt which extends around the periphery of the apparatus 10.

Figure 2:
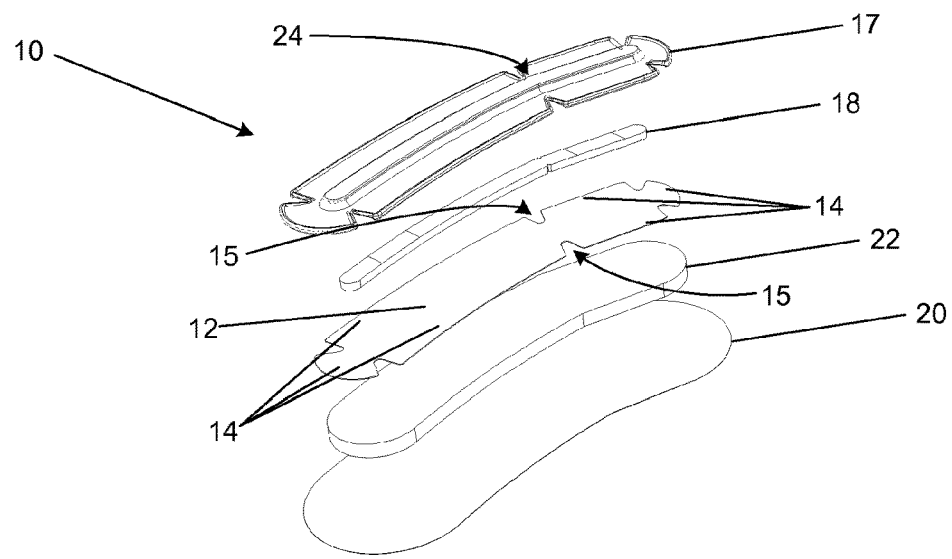
FIG. 2 is a perspective exploded view of the apparatus of FIG. 1.

As illustrated in FIGS. 1 and 2, the apparatus 10 has a longitudinally extending central portion 16 which is substantially rigid. In a preferred embodiment, a stiffener 18 is provided to impart the required rigidity to the longitudinally extending central portion 16. In an alternative embodiment, the longitudinally extending central portion 16 may be integrally formed from a suitable material which imparts the desired rigidity. The longitudinally extending central portion 16 provides general longitudinal rigidity to the apparatus 10 and is configured for transferring a force from a surgical retractor which is used to maintain separation of opposing ends of the severed sternum. The longitudinally extending central portion 16 distributes force from the retractor across the exposed end to reduce fracturing of the sternum. However, longitudinally extending central portion 16 should not be so stiff as to prevent any deformation of the sternum while under retraction, as failure to allow any deformation may lead to other problems such as brachial plexus injuries.

Apparatus 10 further includes a covering 17, which in the described embodiment is formed of a medical grade silicone that encloses or encapsulates the strip 12 and the stiffener 18 to isolate them from the patient. Advantageously, the strip 12 and the stiffener 18 do not come into contact with the patient, thereby allowing non-biocompatible materials to be used in their construction, however, it is envisaged that bio-compatible materials will still be used for the strip 12 and stiffener 18. Also, the covering 17 provides the apparatus with a soft, smooth surface that can be easily handled and manipulated by the surgeon.

In the described embodiment, the strip 12 is formed of aluminium and is 0.3 mm thick. It will be appreciated that the thickness of the material used for the strip 12 may be varied according to the properties of the selected material. The thickness, grade and type of material used may also be varied according to a desired rigidity of the strip 12 so that the pliable portions 14 are sufficiently flexible, bendable or able to be plastically deformed over sides of the exposed end so as to retain or clamp the strip 12 against the exposed end.

In the described embodiment, the stiffener 18 is also formed of aluminium and is between 2.0 mm and 3.0 mm thick. It is envisaged that an aluminium stiffener that is 2.5 mm thick would be ideal, as would a stainless steel stiffener that is 2.0 mm thick, however, other materials may similarly be used.

The covering 17 is formed using overmould techniques in which the strip 12 and the stiffener 18 are placed in an injection moulding tool and the covering is formed around them. In the described embodiment, silicone is used due to its well accepted biocompatibility properties, though it will be appreciated that other polymers/plastic materials may similarly be used.

The stiffener 18 may be fixed to the strip 12 before insertion into the injection moulding tool such as by gluing or using mechanical fixing methods. Alternatively, the strip 12 and the stiffener 18 may be clamped together in the injection moulding tool. Also, the strip may be of unitary construction and have a thicker central section which is much less pliable than thinner outer portions that can be easily bent around sides of the sternum.

Figure 3:
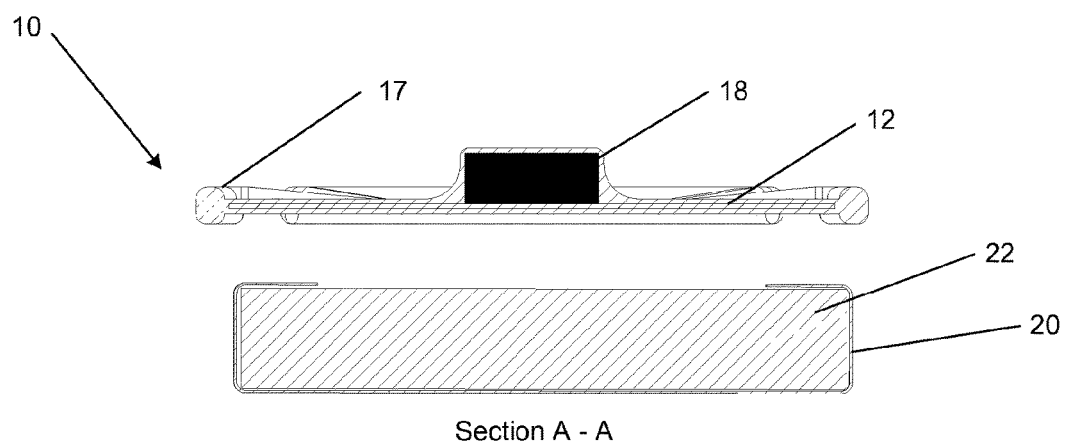
FIG. 3 is a sectional view of the apparatus of FIG. 1, the apparatus being in a partially exploded state.

FIG. 3 illustrates a partially exploded cross sectional view of apparatus 10 in which it can be seen that the strip 12 and the stiffener 18 are enclosed or encapsulated in the cover 17. Although the strip 12 and the stiffener 18 are shown to be encapsulated together, it will be appreciated that they may be separately covered and otherwise joined during assembly. Furthermore, the apparatus 10 is shown as being constructed in a certain order that could be modified, for example the stiffener 18 may be disposed below the strip 12 prior to covering 17 being applied.

The apparatus 10 further comprises a compressible layer 22 between the haemostatic material 20 and the strip 12 to promote apposition between the haemostatic material 20 and the exposed sternal end. The compressible layer 22 may be in the form of an expandable foam material which will contour to the shape and size of the hemi-sternum. The compressible layer 22 is wrapped in a layer of haemostatic material 20 and fixed to the cover 17 to form an assembly, using adhesive for example. The haemostatic material 20 is arranged to be received against the exposed sternal end to promote physiological sternal haemostasis. The haemostatic material 20 can be formed from an oxidised cellulose polymer, such as Surgicel.

The apparatus 10 further comprises an intermediate hinge 24 to provide for longitudinal flexing of the apparatus 10. The intermediate hinge 24 is disposed in a location generally corresponding to a manubriosternal joint of the sternum, and divides apparatus 10 into two portions, a longer lower portion corresponding to the body of the sternum, and a shorter upper portion corresponding to the manubrium. In the described embodiment, apparatus 10 has a curved appearance, with the lower portion of the apparatus being angled approximately 14° to the upper portion of apparatus 10. It is envisaged that an apparatus having an angle between 10° and 18° would be suitable for most patients' sternums. When a retractor is used to separate the ends of the sternum, the sternum can flex about the manubriosternal joint, thereby increasing the possibility of separation of the apparatus 10 from the sternum leading to bleeding around this area. By providing an intermediate hinge 24, the apparatus 10 can accommodate for movement of the sternum, thereby improving apposition between the haemostatic material 20 and/or compressible layer 22 and the exposed sternal end.

The intermediate hinge 24 may be formed by incorporating areas of weakness into the apparatus 10 in the form of notches 15 formed in the strip 12. As illustrated in FIG. 2, the pliable portions 14 and the stiffener 18 are both necked in at this point so as to weaken the apparatus 10 in an area proximal to the intermediate hinge 24 so that the apparatus 10 can be bent as required during use. The stiffener may also be formed with a transverse notch 19 to allow for longitudinal flexing. The pliable portions 14 are necked in about the hinge to allow them to neatly deform without buckling, thereby improving retention of the apparatus 10 against the sternal end.

In the described embodiment the strip 12 is shown to be of unitary construction for convenience, though it will be appreciated that the strip 12 may be formed from a plurality of discrete elements joined together. Similarly, the strip 12 and the pliable portions 14 are illustrated as being an integral unit, though it will be appreciated that they may be formed of separate components fixed together.

Apparatus 10 is shown as being generally planar. When a surgical retractor is used to separate the exposed ends, it has been observed that the sternum tends to twist, thereby possibly reducing the effectiveness of a planar apparatus. It is therefore envisaged that the apparatus 10 may not be formed completely flat, but formed with a bow or twist to accommodate deflection of the sternum under retraction. Alternatively, the apparatus 10 may be manufactured so as to retain a degree of flexibility which would allow the apparatus to address this sternal variation.

Figure 4:
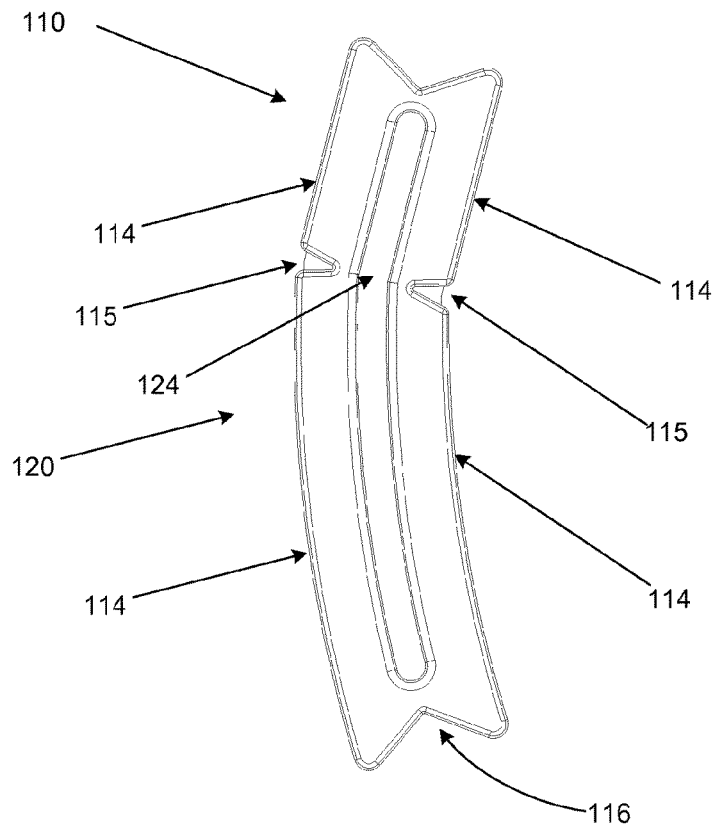
FIG. 4 is a plan view of an apparatus for covering an exposed end of a severed sternum of another embodiment of the invention.
Figure 5:
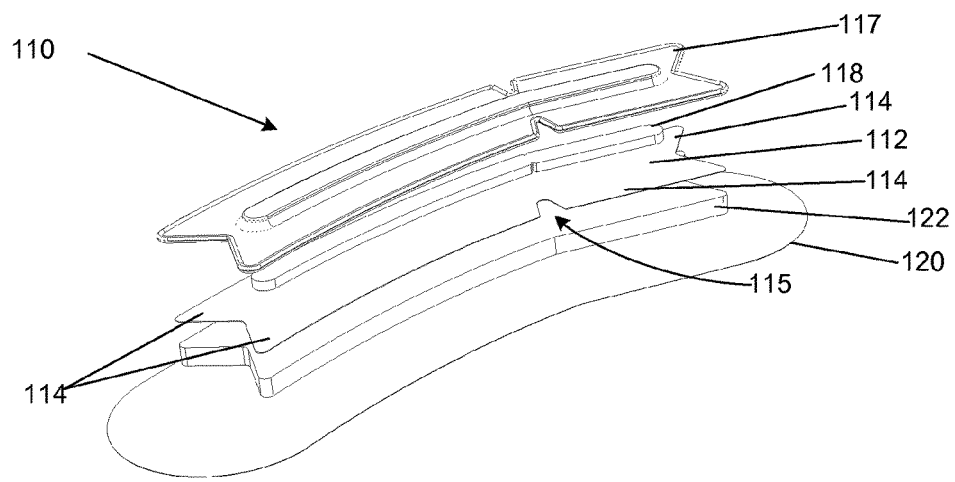
FIG. 5 is a perspective exploded view of the apparatus of FIG. 4.

Another apparatus 110 according to another preferred embodiment of the present invention is shown in FIGS. 4 and 5. The apparatus 110 is also configured for covering an exposed end of a severed sternum and is constructed similarly to apparatus 10 so that the preceding description applies to this embodiment via similarly numbered components each incremented by 100. As can be seen in FIG. 4, the pliable portions 114 are differently configured so as to remove the end portions so that the apparatus 110 is only fixed to sides of the exposed end.

Figure 6:
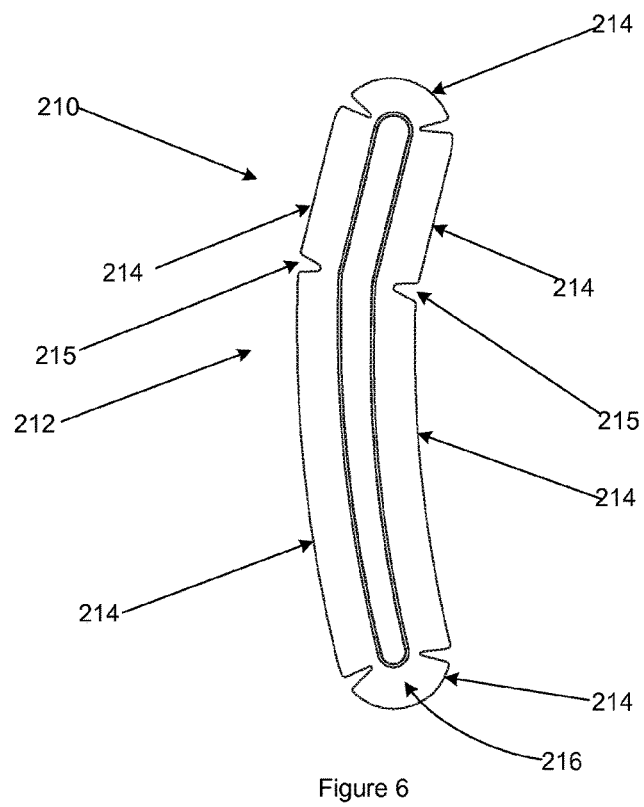
FIG. 6 is a plan view of an apparatus for covering an exposed end of a severed sternum of another embodiment of the invention.
Figure 7:
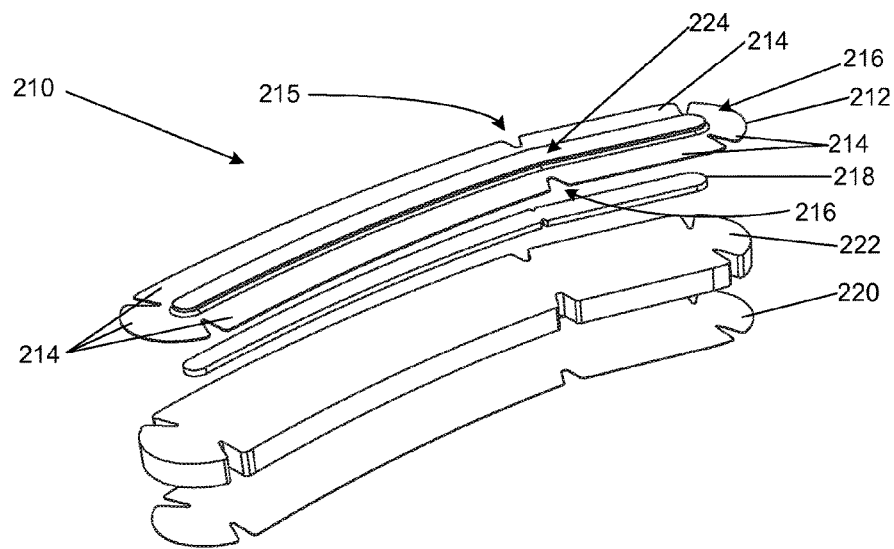
FIG. 7 is a perspective exploded view of the apparatus of FIG. 6.

Another apparatus 210 according to another preferred embodiment of the present invention is shown in FIGS. 6 and 7. The apparatus 210 is also configured for covering an exposed end of a severed sternum and is constructed similarly to apparatuses 10, 110 so that the preceding description applies to this embodiment via similarly numbered components each incremented by 100.

The rigid portion 216 of apparatus 210 is formed by forming a cavity in the strip 212 in which a stiffener 218 is received. Such a configuration provides that the pliable portions 214 form part of the strip 212 that is integrally stiffened so that the strip can be rigidly and securely fixed directly to the exposed end. It will be appreciated that the other similar configurations are possible and fall within the scope of the invention. For example, although the pliable portions 214 are shown as being part of the strip 212 it will be appreciated that other configurations in which the pliable portions are formed separately from the strip 212 are also possible. An example of such an arrangement is a plurality of pliable strips that can be deformed so as to form C-shaped clamps that are configured to fit over the strip 212 and engage the exposed end to retain the strip in position. Furthermore, the stiffener 218 may be otherwise fixed to the strip 212 such as by gluing or using mechanical fixing methods. Also, the strip may be of unitary construction and have a thicker central section which is much less pliable than thinner outer portions that can be easily bent around sides of the sternum.

In the described embodiment, the strip 212 is formed of stainless steel, the grade and thickness of which are selected so that the pliable portions 214 are sufficiently malleable and formable so that they can easily be bent or folded over sides of the exposed end. Stainless steel may be a convenient material for use due to biocompatibility properties. However, it is envisaged that other malleable metals such as copper or aluminium may similarly be used with appropriate treatment or surface coatings.

Figure 8:
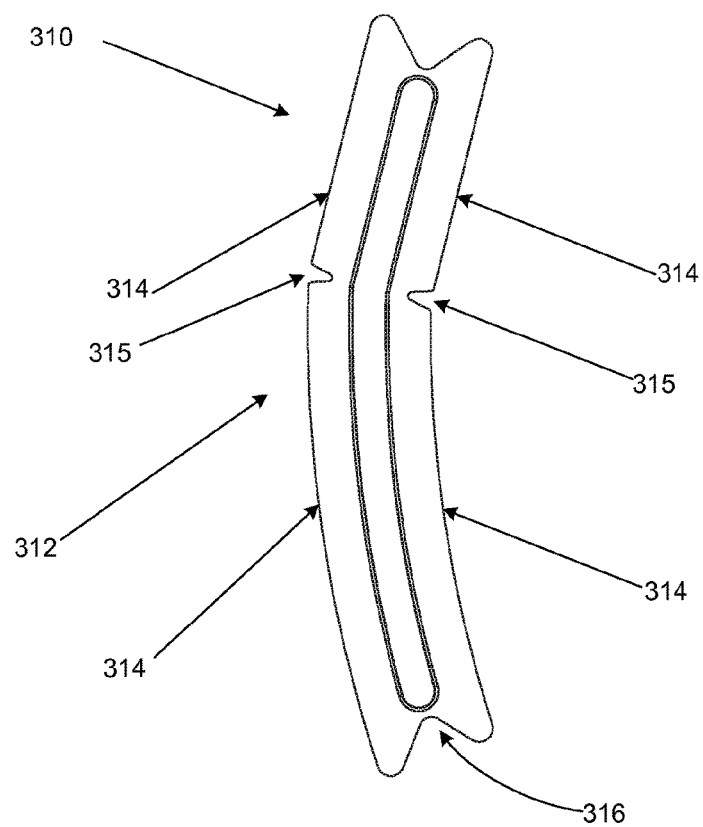
FIG. 8 is a plan view of an apparatus for covering an exposed end of a severed sternum of another embodiment of the invention.
Figure 9:
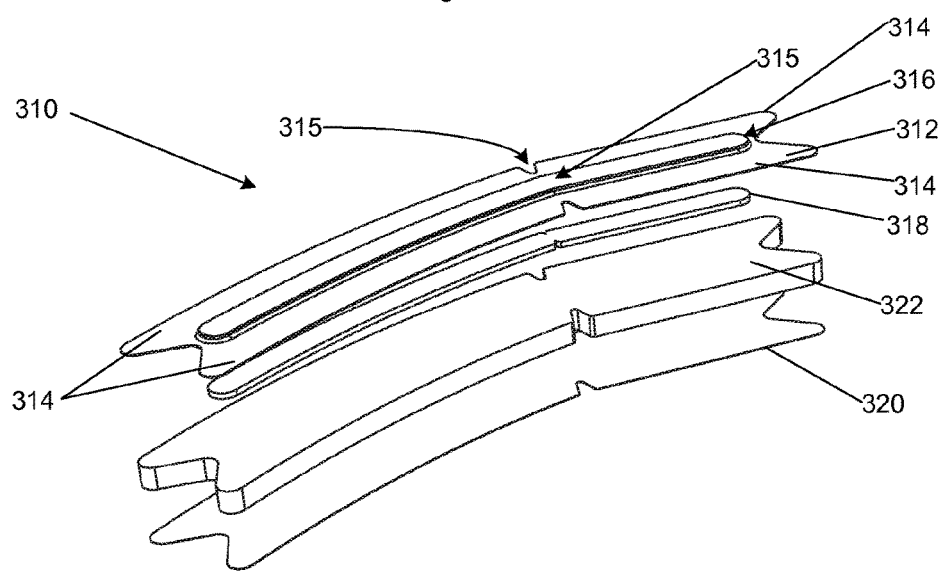
FIG. 9 is a perspective exploded view of the apparatus of FIG. 8.

Another apparatus 310 according to another preferred embodiment of the present invention is shown in FIGS. 8 and 9. The apparatus 310 is also configured for covering an exposed end of a severed sternum and is constructed similarly to apparatuses 10, 110, 210 so that the preceding description applies to this embodiment via similarly numbered components each incremented by 100. As can be seen in FIG. 8, the pliable portions 314 are configured in a manner similar to pliable portions 114 of FIG. 4. In this regard, the pliable portions 314 are configured so as to remove their end portions so that the apparatus 310 is only fixed to sides of the exposed end.

Each of apparatus 10, 110, 210, 310 is generally illustrated as being constructed in layers, though it will be appreciated that at least some of these layers may be combined to form an apparatus of unitary construction. In this regard, the strip, the pliable portions and the rigid portion can be integrally formed. In one example, these parts are pressed, stamped or otherwise formed so that a member having a stiff central section and pliable outer portions is provided.

In another example, the apparatus comprises a pliable mesh material suspended in a polymer matrix. The polymer is preferably a medical grade silicone and the pliable mesh is preferably formed of a metallic material, such as stainless steel. Advantageously, because it is the polymer material that comes into contact with the exposed end, selection of a material that will not have an adverse reaction with the patient can be easily achieved with the apparatus. In such an embodiment, a stiffener may also be incorporated into the matrix to distribute the load of the retractor for the reasons discussed above.

It is envisaged that the apparatus 10, 110, 210, 310 would be manufactured in different sizes, or a single size that may be adjusted to suit various sized sternums. In one preferred embodiment, the applicant has found that it is possible to accommodate most sternum sizes with a range of 2 to 4 differently sized apparatuses which correspond to a predetermined size range of sternums. For example, the apparatus may be provided in a Large size suitable for sternums in the range of 175 mm-200 mm, a Medium size suitable for sternums in the range of 150 mm-175 mm, a Small size suitable for sternums in the range of 125 mm-150 mm, and a Extra-Small size suitable for sternums under 125 mm in length. The size of the pliable portions 14 may vary in accordance with the size of the apparatus. For example, the Large apparatus may have pliable portions that extend between 10 and 20 mm from the strip, while the Extra-Small apparatus may have pliable portions that extend between 5 and 12 mm from the strip.

Figure 10C:
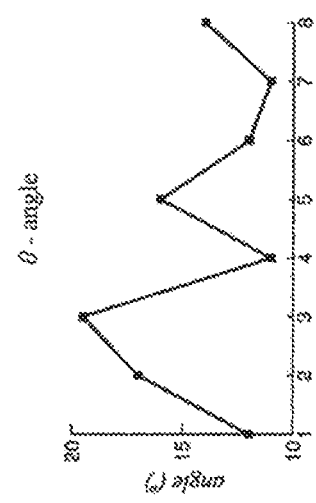
FIGS. 10A to 10E represent a sample of eight subjects having medium-sized sternums.
Figure 10E:
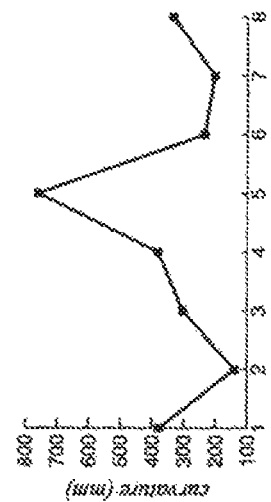
Figure 10B:
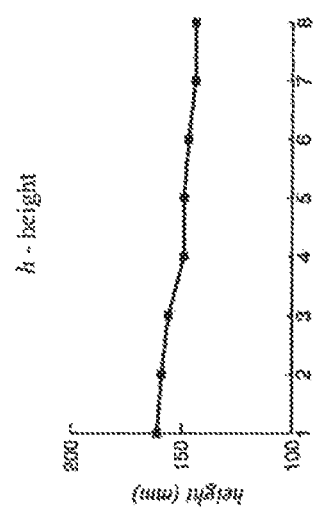
Figure 10D:
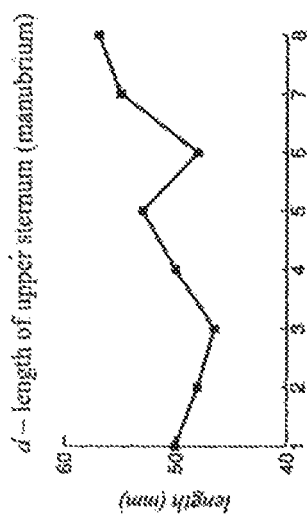
Figure 10A:
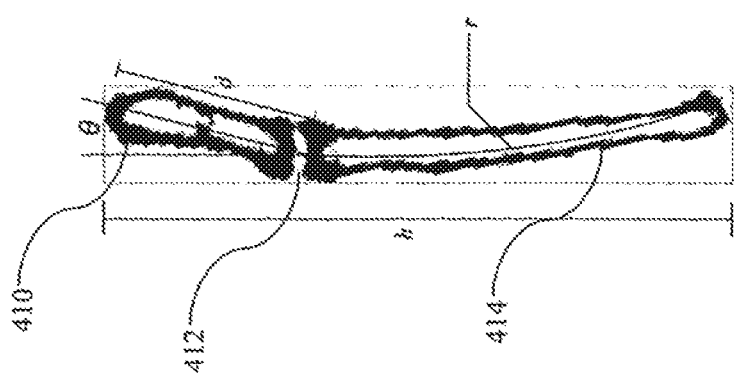
Figure 11B:
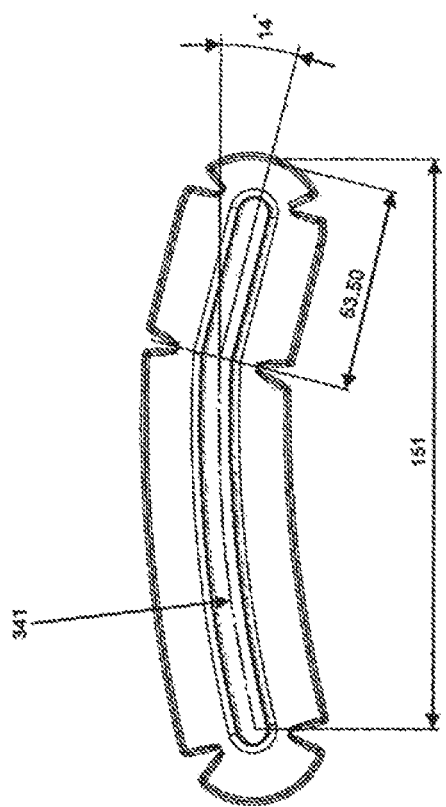
FIGS. 11A and 11B illustrate an apparatus suitable for an average medium-sized sternum.
Figure 11A:
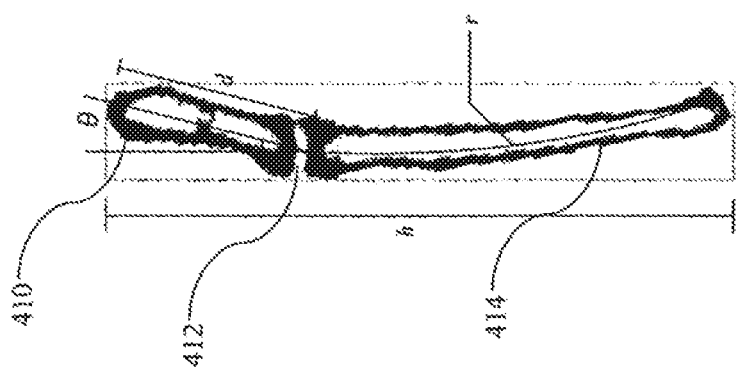

The predetermined size ranges were established by conducting a study of sternal sizes. For example, FIGS. 10A to 10E represent a study of eight subjects having medium-sized sternums. In this study, the average height (h) of the apparatus required to cover the sternum, the angle (θ) between the manubrium and lower sternum, length of the manubrium (d) and radius of curvature (r) of the lower sternum were assessed. FIG. 10A is a side-view of a cut sternum displaying the relationship between these characteristics, as well as showing the manubrium 410, manubriosternal joint 412, and lower sternum 414. Each measured characteristic is shown plotted in FIGS. 10B to 10E. From the sample of eight subjects, it was determined that the characteristics of the apparatus suitable to cover the average medium-sized sternum is as follows: h=151 mm; θ=14°; d=53.5 mm and r=341 mm, as shown in FIGS. 11A and 11B. Thus, an apparatus having a height (h) of 150±25 mm would be suitable for the vast majority of medium-sized sternums. Similar studies were conducted for the Large, Small and Extra-Small sternum sizes. These studies indicate that a suitable height (h) for the Large apparatus is 175±25 mm, for the Small apparatus is 125±25 mm and for the Extra-Small apparatus 100±25 mm.

In an alternative preferred embodiment, the apparatus may be provided in a Large size suitable for sternums in the range of 150 mm-200 mm, and a Small size suitable for sternums in the range of 100 mm-150 mm. In a further alternative embodiment, the apparatus may be provided in a single size which may be adjusted to suit various sized sternums. For example, the apparatus may be provided in the form of a strip which can be cut to length depending on the size of a patient's sternum.

The apparatus may be provided as a pair, one piece for each of the opposing ends of a severed sternum. A disposable ruler may be provided separately for measuring the exposed end to determine the size of the apparatus required for a particular patient. It is envisaged that a surgeon would use the ruler to measure the size of the exposed end and, based on the size of the end, either cut the apparatus to the appropriate size or select an appropriately sized apparatus for use.

Figure 12:
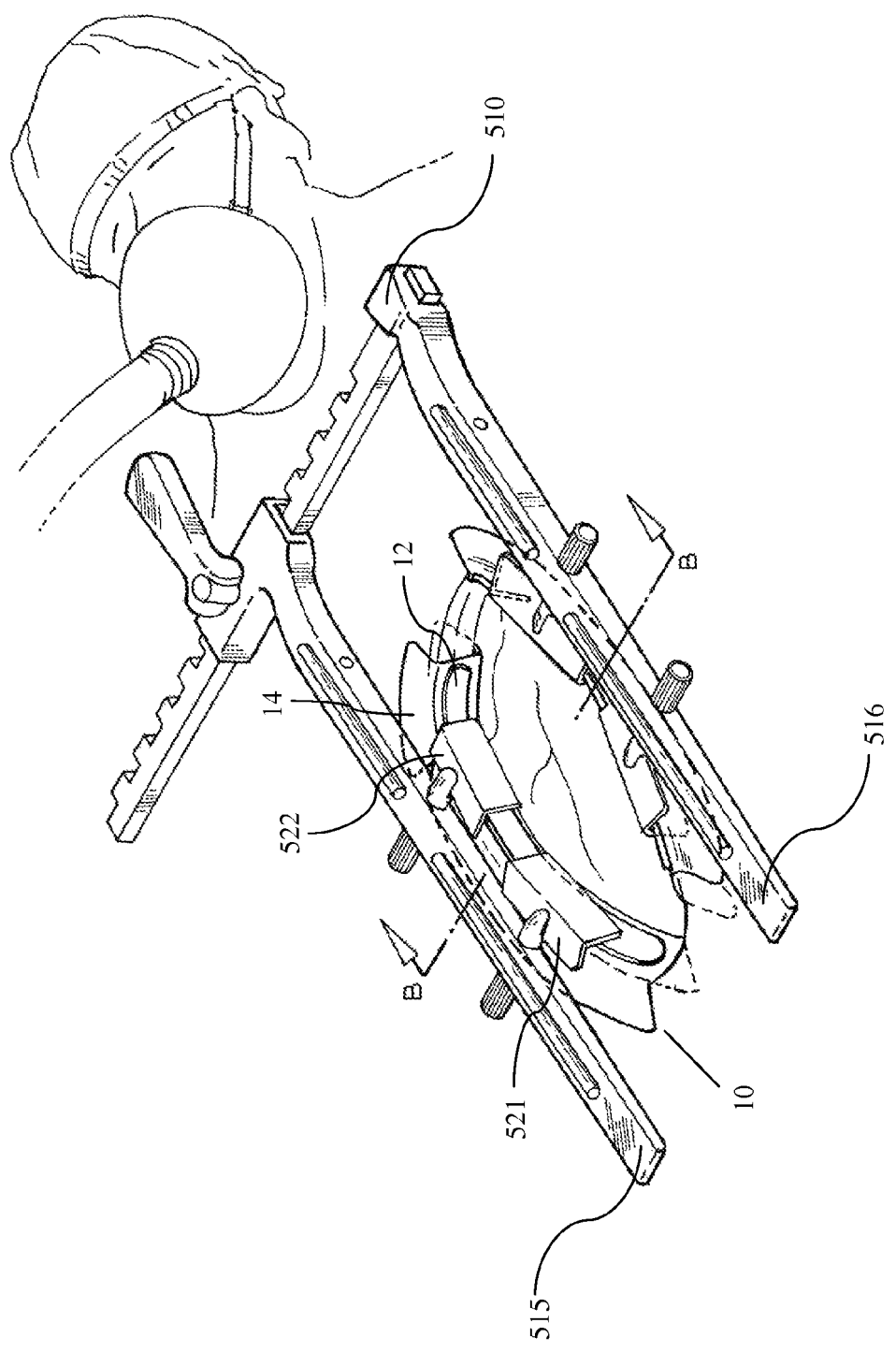
FIG. 12 is a perspective view illustrating the apparatus in use following a median sternotomy incision.

FIG. 12 is a perspective view illustrating the apparatus in use following a median sternotomy incision. Once a vertical incision is made along the sternum, and the sternum has been divided, an apparatus 10, having a strip 12 which is operative to cover an exposed end of the sternum is inserted at the site of the incision. The strip 12 is placed against the exposed end of the sternum and the pliable portions 14 are deformed or bent over sides of the exposed end to retain the strip against the exposed end to reduce bleeding. A retractor 510 is then inserted, and arranged such that the strip 12 sits between the exposed end and retractor blades 521 and 522 which descend from arm 515 of the retractor. Retractor 510 generally includes a pair of opposing arms 515 and 516 adapted to engage opposite sides of a sternal incision, and a drive mechanism constructed to force the arms, and thus the sternum apart. Using the drive mechanism, the sternum may be spread to the desired opening, thus providing surgical access to the thoracic cavity.

Prior to opening the retractor 510, an exposed end of the hemi-sternum faces the exposed end of the other hemi-sternum, which is directed medially. After the retractor 510 is opened, the exposed ends of the hemi-sternum that are cranial or caudal to the retractor blades 521 and 522 rotate to a degree so that the cut surfaces in these areas of the hemi-sternum face antero-medially (towards the ceiling with the patient lying supine) whilst the cut surface of the hemi-sternum between retractor blades 521 and 522 substantially faces the exposed end of the other hemi-sternum, which is directly medially. Furthermore, when the retractor 510 is opened and the exposed ends are spread apart, the hemi-sternum curves along the length of the incision, and can bow so that the sternum becomes more concave on its medial aspect.

Figure 13:
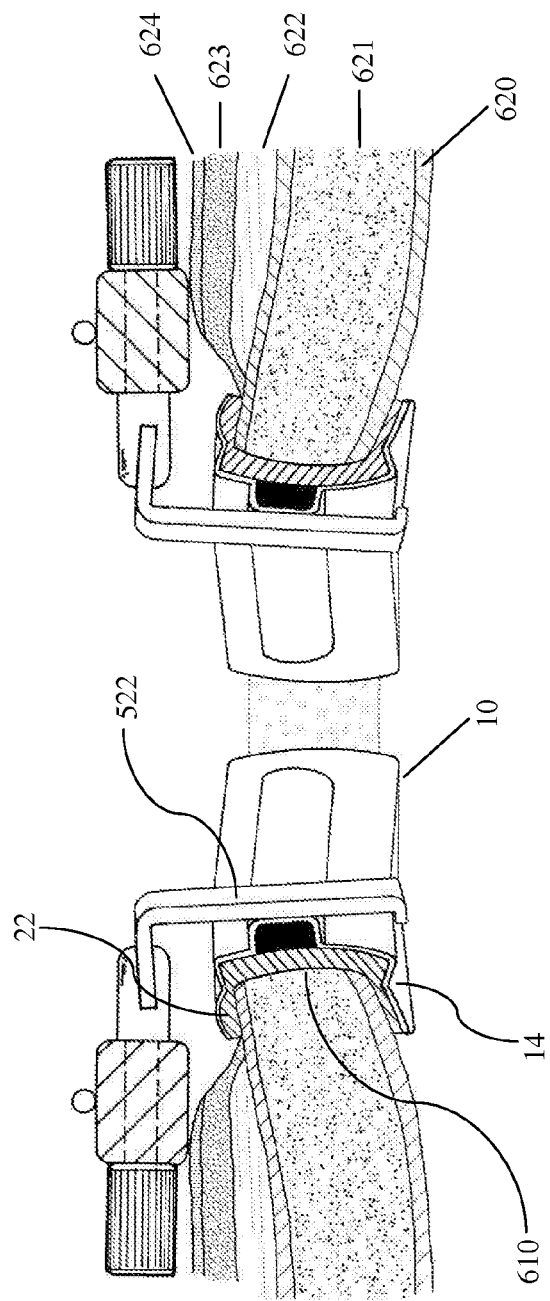
FIG. 13 is a view taken along line B-B shown in FIG. 12.

As can be seen in FIG. 13, apparatus 10 sits between the exposed end 610 of the sternum and retractor blade 522, and is able to deform in the same manner as the exposed end of the sternum, both longitudinally and latitudinally. Apparatus 10 effectively covers the exposed surfaces of the sternal cortex 620 and sternal medulla 621. Pectoralis major muscle 622, adipose tissue 623, and dermis 624 are positioned more laterally after sternotomy and are usually not covered by apparatus 10. In some situations apparatus 10 may cover some of pectoralis major muscle 622 and adipose tissue 623. By deforming pliable portions 14 of the apparatus around the exposed ends, strip 12 and compressible layer 22 are retained against the exposed ends, and the flow of blood from the exposed ends is stopped or reduced.

The method can include the step of measuring the exposed end and selecting an appropriately sized apparatus from a selection of differently sized apparatuses. The selection of differently sized apparatuses may include 2 to 4 differently sized apparatuses corresponding to common size ranges of sternums. The exposed end can be measured using a disposable ruler, or other similar measuring apparatus such as a stencil.

Although the invention has been disclosed in its preferred forms, it is to be understood that the above embodiments have been provided only by way of exemplification of this invention, and that further modifications and improvements thereto, as would be apparent to persons skilled in the relevant art, are deemed to fall within the broad scope and ambit of the current invention described and claimed herein. For example, the apparatus may be formed from a plurality of discrete elements. Such a construction would allow those elements which were in contact with a patient to be discarded, and be replaced with that either new elements or sterilised re-usable elements.

The reference to any prior art in this specification is not, and should not be taken as, an acknowledgement or any form of suggestion that the prior art forms part of the common general knowledge of the person skilled in the relevant technical field.

The invention claimed is:

1. An apparatus for covering an exposed end of a severed sternum, the apparatus comprising:
    an inner layer configured to contact surfaces of the exposed end of the severed sternum and to reduce bleeding from the exposed end;

a pliable layer having a pliable layer width and a pliable layer length, the pliable layer having first and second elongated sides along the pliable layer length, each of the first and second elongated sides having a plurality of notches disposed at intervals along the pliable layer length of the pliable layer, wherein the pliable layer is configured to be bent, during surgery, longitudinally at the plurality of notches to shape the pliable layer to the curvature of the exposed sternum and laterally to shape the pliable layer to a width of the exposed sternum, wherein the pliable layer is plastically deformable such that it retains the bent shape and the pliable layer is attached to the inner layer via an adhesive;

a spine disposed longitudinally along the pliable layer length of the pliable layer and configured to provide support to the pliable layer, the spine disposed adjacent a surface of the pliable layer and non-embedded in the pliable layer; and an outer covering disposed over the spine and the pliable layer and entirely covering the spine and the pliable layer, such that the outer covering on the spine is configured to be engaged by a retractor and the spine distributes forces from the retractor along the length of the pliable layer.

2. The apparatus of claim 1, wherein the inner layer comprises a compressible layer disposed adjacent the pliable layer.

3. The apparatus of claim 1, wherein the inner layer comprises:
a compressible layer disposed adjacent the pliable layer; and
an inner fabric disposed over the compressible layer, wherein the compressible layer is configured to be compressed to apposition the inner fabric on the exposed end of the severed sternum.

4. The apparatus of claim 3, wherein the inner fabric includes a haemostatic material configured to at least reduce the bleeding from the severed end.

5. The apparatus of claim 1, wherein the inner layer has an inner layer length and an inner layer width, such that the inner layer is configured to be positioned to contact the exposed end of the severed sternum with the inner layer length coincident with a length of the severed sternum.

6. The apparatus of claim 5, wherein the pliable layer and the inner layer are configured to be bent to conform to the exposed end of the severed sternum and the pliable layer width and the inner layer width are configured to be sufficient to cover the sternal cortex and the sternal medulla surfaces of the severed sternum without engaging at least one of the pectoralis major muscle, adipose tissue, and dermis.

7. The apparatus of claim 1, wherein the pliable layer includes a strip and pliable portions extending away from the strip.

8. The apparatus of claim 7, wherein the strip is centrally located in the pliable layer along the pliable layer length, and the pliable portions extend equal distances away from the strip on each side of the strip.

9. The apparatus of claim 1, wherein the spine has a spine length and the spine includes a spine notch disposed along the spine length of the spine, wherein the spine notch is coincident with one of the plurality of notches in the pliable layer.

10. An apparatus for at least partially covering an exposed end of a severed sternum of a patient after a sternotomy, wherein the exposed end has an exposed length and includes sternal cortex and sternal medulla surfaces of the severed sternum and the sternotomy exposes pectoralis major muscle, adipose tissue, and dermis of the patient, the apparatus comprising:

an inner layer having an inner layer length and an inner layer width and configured to be positioned with the inner layer length coincident with the exposed length of the exposed end to contact the sternal cortex and the sternal medulla surfaces of the exposed end and to reduce bleeding from the sternal medulla surface;

a pliable layer attached to the inner layer and positioned with a pliable layer length coincident with the inner layer length and a pliable layer width coincident with the inner layer width, the pliable layer having a first side and a second side along the pliable layer length, the first side having a first plurality of notches disposed at intervals along the pliable layer length and the second side having a second plurality of notches disposed at intervals along the pliable layer length, wherein the pliable layer and the inner layer are configured to be formed, during surgery, at the first plurality of notches and the second plurality of notches to shape the pliable layer and the inner layer to the curvature of the severed sternum and to conform the pliable layer and the inner layer to the exposed end of the severed sternum such that the pliable layer width and the inner layer width are sufficient to cover the sternal cortex and the sternal medulla surfaces of the exposed end without engaging at least one of the pectoralis major muscle, adipose tissue, and dermis, wherein the pliable layer is plastically deformable such that it retains the formed shape; and an outer covering entirely covering outer surfaces of the pliable layer, such that the outer covering is configured to be engaged by a retractor and the pliable layer is configured to distribute forces from the retractor along the pliable layer length and the severed sternum.

11. The apparatus of claim 10, wherein the inner layer comprises a compressible layer disposed adjacent the pliable layer.

12. The apparatus of claim 10, wherein the inner layer comprises:
a compressible layer disposed adjacent the pliable layer; and
an inner fabric disposed on the compressible layer, wherein the compressible layer is configured to be compressed to apposition the inner fabric on the exposed end of the severed sternum.

13. The apparatus of claim 12, wherein the inner fabric includes a haemostatic material configured to at least reduce the bleeding from the severed end.

14. The apparatus of claim 10, comprising a spine disposed longitudinally on the pliable layer coincident with the pliable layer length and configured to provide support to the pliable layer, the spine disposed adjacent a surface of the pliable layer and non-embedded in the pliable layer.

15. The apparatus of claim 14, wherein the outer covering covers the spine on the pliable layer and the outer covering over the spine is configured to engage the retractor, such that the spine distributes forces from the retractor along the pliable layer length and the severed sternum to reduce fracturing of the severed sternum.

16. A method of at least reducing bleeding from one or more exposed ends of a severed sternum of a patient after a sternotomy, wherein each of the one or more exposed ends includes sternal cortex and sternal medulla surfaces and the sternotomy exposes pectoralis major muscle, adipose tissue, and dermis of the patient, the method comprising:

inserting an apparatus between two exposed ends of the severed sternum;

situating an inner layer of the apparatus longitudinally along the sternal cortex and the sternal medulla surfaces of one of the two exposed ends; and forming, during surgery, the inner layer and a pliable layer attached to the inner layer, the pliable layer having a pliable layer width and a pliable layer length, the pliable layer having first and second elongated sides along the pliable layer length, each of the first and second elongated sides having a plurality of notches disposed at intervals along the pliable layer length, such that the inner layer and the pliable layer are formed during surgery at the plurality of notches over the one of the two exposed ends to position the inner layer on the sternal cortex and the sternal medulla surfaces of the one of the two exposed ends and further formed during surgery to laterally position the inner layer over the sternal cortex of the severed sternum without engaging at least one of the pectoralis major muscle, adipose tissue, and dermis, the pliable layer being plastically deformable such that the pliable layer retains the formed shape that the pliable layer is formed into during surgery.

17. The method of claim 16, wherein situating an inner layer and forming the inner layer and a pliable layer comprises compressing a compressible layer of the inner layer to position the inner layer adjacent the sternal cortex and the sternal medulla surfaces.

18. The method of claim 17, wherein situating an inner layer and forming the inner layer and a pliable layer comprises positioning an inner fabric on the compressible layer adjacent the sternal cortex and the sternal medulla surfaces.

19. The method of claim 16, comprising positioning the pliable layer with the pliable layer length coincident with a length of the exposed end, such that an outer covering disposed over the pliable layer is configured to be engaged by a retractor and the pliable layer distributes forces from the retractor along the pliable layer length of the pliable layer to reduce fracturing of the severed sternum.

20. The method of claim 16, comprising positioning the pliable layer and a spine on the pliable layer with the pliable layer length coincident with a length of the exposed end, the spine disposed adjacent a surface of the pliable layer and non-embedded in the pliable layer, such that an outer covering disposed over the spine and the pliable layer is configured to be engaged by a retractor and the spine distributes forces from the retractor along the pliable layer length of the pliable layer to reduce fracturing of the severed sternum.

* * * * *